United States Patent
Freitag

(10) Patent No.: US 7,252,680 B2
(45) Date of Patent: Aug. 7, 2007

(54) REMOVABLE ESSENTIALLY CYLINDRICAL IMPLANTS

(75) Inventor: Lutz Freitag, Hemer (DE)

(73) Assignee: Alveolus, Inc., Charlotte, NC (US)

( * ) Notice: Subject to any disclaimer, the term of this patent is extended or adjusted under 35 U.S.C. 154(b) by 0 days.

(21) Appl. No.: 10/475,232

(22) PCT Filed: Apr. 5, 2002

(86) PCT No.: PCT/DE02/01244

§ 371 (c)(1),
(2), (4) Date: Nov. 24, 2003

(87) PCT Pub. No.: WO02/083037

PCT Pub. Date: Oct. 24, 2002

(65) Prior Publication Data

US 2004/0116996 A1 Jun. 17, 2004

(30) Foreign Application Priority Data

Apr. 18, 2001 (DE) ................ 101 18 944

(51) Int. Cl.
*A61F 2/06* (2006.01)
*A61F 11/00* (2006.01)
(52) U.S. Cl. ............... 623/1.12; 606/108; 606/194
(58) Field of Classification Search ............ 623/1.1, 623/1.11, 1.12, 1.22, 1.3, 1.49–1.54, 11.11, 623/13.13–13.15, 23.64–23.69; 606/191, 606/194, 195, 198, 108
See application file for complete search history.

(56) References Cited

U.S. PATENT DOCUMENTS

| | | |
|---|---|---|
| 3,196,876 A | 7/1965 | Roberts et al. |
| 3,818,511 A | 6/1974 | Goldberg et al. |
| 4,343,048 A | 8/1982 | Ross et al. |
| 4,441,215 A | 4/1984 | Kaster |
| 4,606,330 A | 8/1986 | Bonnet |
| 4,655,771 A | 4/1987 | Wallsten |
| 4,665,906 A | 5/1987 | Jervis |
| 4,680,031 A | 7/1987 | Alonso |
| 4,733,665 A | 3/1988 | Palmaz |
| 4,739,762 A | 4/1988 | Palmaz |
| 4,743,251 A | 5/1988 | Barra |
| 4,800,882 A | 1/1989 | Gianturco |
| 4,820,262 A | 4/1989 | Finney |
| 4,820,298 A | 4/1989 | Leveen et al. |
| 4,856,516 A | 8/1989 | Hillstead |

(Continued)

FOREIGN PATENT DOCUMENTS

DE 197 03 482 A 8/1998

(Continued)

OTHER PUBLICATIONS

U.S. Appl. No. 08/246,320, filed May 19, 1994, Burnmeister et al.

*Primary Examiner*—David J Isabella
(74) *Attorney, Agent, or Firm*—Alston & Bird LLP; Tony D. Alexander, Esq.

(57) ABSTRACT

The invention relates to removable, essentially cylindrical implants which are characterized in that they can be reduced in diameter and are wrapped once or several times at one or more levels by one or more elastic, thin wire-shaped structure(s) (2*a*, 2*b*) which include(s) a catch device (3*a*, 3*b*) at least on one end thereof.

16 Claims, 5 Drawing Sheets

U.S. PATENT DOCUMENTS

Figure 1:
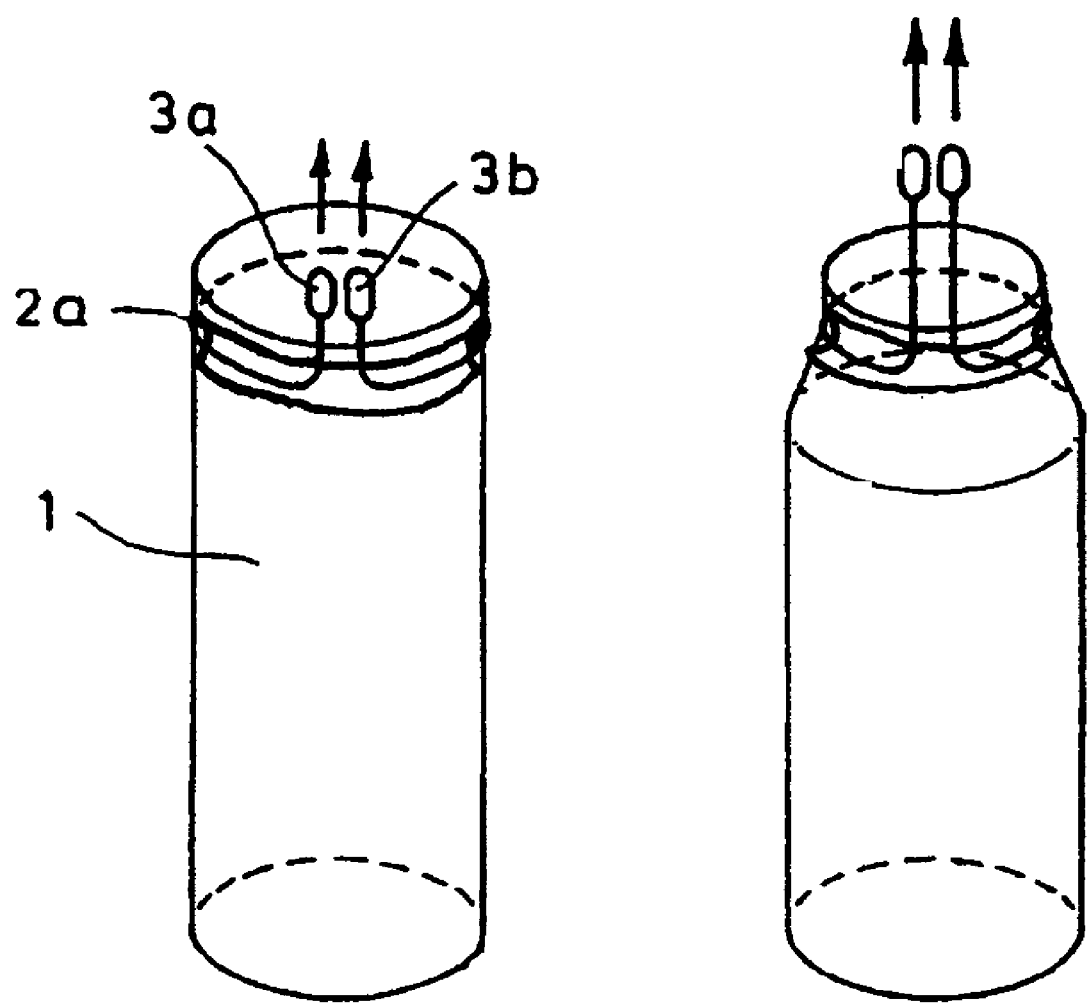

| | | | |
|---|---|---|---|
| 4,886,062 A | 12/1989 | Wiktor | |
| 4,893,623 A | 1/1990 | Rosenbluth | |
| 5,019,085 A | 5/1991 | Hillstead | |
| 5,032,128 A | 7/1991 | Alonso | |
| 5,035,706 A | 7/1991 | Giantureo et al. | |
| 5,061,275 A | 10/1991 | Wallsten et al. | |
| 5,064,435 A | 11/1991 | Porter | |
| 5,067,957 A | 11/1991 | Jervis | |
| 5,073,694 A | 12/1991 | Tessier et al. | |
| 5,102,417 A | 4/1992 | Palmaz | |
| 5,104,404 A | 4/1992 | Wolff | |
| 5,159,920 A | 11/1992 | Condon et al. | |
| 5,190,546 A | 3/1993 | Jervis | |
| 5,195,984 A | 3/1993 | Schatz | |
| 5,229,431 A | 7/1993 | Pinchuk | |
| 5,249,585 A | 10/1993 | Turner et al. | |
| 5,292,331 A | 3/1994 | Boneau | |
| 5,320,617 A | 6/1994 | Leach | |
| 5,345,057 A | 9/1994 | Muller | |
| 5,354,309 A | 10/1994 | Schnepp-Pesch et al. | |
| 5,356,423 A | 10/1994 | Tihon et al. | |
| 5,383,892 A | 1/1995 | Cardon et al. | |
| 5,383,925 A | 1/1995 | Schmitt | |
| 5,409,453 A | 4/1995 | Lundquist et al. | |
| 5,421,955 A | 6/1995 | Lau et al. | |
| 5,443,498 A | 8/1995 | Fontaine | |
| 5,449,373 A | 9/1995 | Pinchasik et al. | |
| 5,514,093 A | 5/1996 | Ellis et al. | |
| 5,514,154 A | 5/1996 | Lau et al. | |
| 5,534,287 A | 7/1996 | Lukic | |
| 5,540,713 A | 7/1996 | Schnepp-Pesch et al. | |
| 5,549,644 A | 8/1996 | Lundquist et al. | |
| 5,562,725 A | 10/1996 | Schmitt et al. | |
| 5,575,818 A | 11/1996 | Pinchuk | |
| 5,588,949 A | 12/1996 | Taylor et al. | |
| 5,591,157 A | 1/1997 | Hennings et al. | |
| 5,591,197 A | 1/1997 | Orth et al. | |
| 5,593,442 A | 1/1997 | Klein | |
| 5,597,378 A | 1/1997 | Jervis | |
| 5,601,591 A | 2/1997 | Edwards et al. | |
| 5,603,698 A | 2/1997 | Roberts et al. | |
| 5,643,312 A | 7/1997 | Fischell et al. | |
| 5,645,559 A | 7/1997 | Hachtman et al. | |
| 5,667,486 A | 9/1997 | Mikulich et al. | |
| 5,667,522 A | 9/1997 | Flomenbilt et al. | |
| 5,674,241 A | 10/1997 | Bley et al. | |
| 5,681,346 A | 10/1997 | Orth et al. | |
| 5,707,386 A | 1/1998 | Schnepp-Pesch et al. | |
| 5,716,393 A | 2/1998 | Lindenberg et al. | |
| 5,725,572 A | 3/1998 | Lam et al. | |
| 5,733,303 A | 3/1998 | Israel et al. | |
| 5,746,692 A | 5/1998 | Bacich et al. | |
| 5,755,776 A | 5/1998 | Al-Saadon | |
| 5,755,781 A | 5/1998 | Jayaraman | |
| 5,759,192 A | 6/1998 | Saunders | |
| 5,766,238 A | 6/1998 | Lau et al. | |
| 5,776,161 A | 7/1998 | Globerman | |
| 5,776,186 A * | 7/1998 | Uflacker | 606/194 |
| 5,780,807 A | 7/1998 | Saunders | |
| 5,782,838 A | 7/1998 | Beyar et al. | |
| 5,807,404 A | 9/1998 | Richter | |
| 5,814,063 A | 9/1998 | Freitag | |
| 5,817,102 A | 10/1998 | Johnson et al. | |
| 5,824,058 A | 10/1998 | Ravenscroft et al. | |
| 5,827,321 A | 10/1998 | Roubin et al. | |
| 5,833,694 A | 11/1998 | Poncet | |
| 5,836,966 A | 11/1998 | St. Germain | |
| 5,843,120 A | 12/1998 | Israel et al. | |
| 5,860,999 A | 1/1999 | Schnepp-Pesch et al. | |
| 5,876,448 A | 3/1999 | Thompson et al. | |
| 5,876,449 A | 3/1999 | Starck et al. | |
| 5,879,370 A | 3/1999 | Fischell et al. | |
| 5,902,333 A | 5/1999 | Roberts et al. | |
| 5,902,475 A | 5/1999 | Trozera et al. | |
| 5,911,732 A | 6/1999 | Hojeibane | |
| 5,922,019 A | 7/1999 | Hankh et al. | |
| 5,922,020 A | 7/1999 | Klein et al. | |
| 5,935,162 A | 8/1999 | Dang | |
| 5,938,682 A | 8/1999 | Hojeibane et al. | |
| 5,971,950 A | 10/1999 | Lopez et al. | |
| 5,972,018 A | 10/1999 | Israel et al. | |
| 5,980,552 A | 11/1999 | Pinchasik et al. | |
| 5,984,964 A | 11/1999 | Roberts et al. | |
| 6,017,365 A | 1/2000 | Von Oepen | |
| 6,019,778 A | 2/2000 | Wilson et al. | |
| 6,022,371 A | 2/2000 | Killion | |
| 6,027,527 A | 2/2000 | Asano et al. | |
| 6,033,435 A | 3/2000 | Penn et al. | |
| 6,042,597 A | 3/2000 | Kveen et al. | |
| 6,048,361 A | 4/2000 | Von Oepen | |
| 6,051,021 A | 4/2000 | Frid | |
| 6,053,941 A | 4/2000 | Lindenberg et al. | |
| 6,056,775 A | 5/2000 | Borghi et al. | |
| 6,059,811 A | 5/2000 | Pinchasik et al. | |
| 6,086,528 A | 7/2000 | Adair | |
| 6,090,115 A | 7/2000 | Beyar et al. | |
| 6,099,560 A | 8/2000 | Penn et al. | |
| 6,106,548 A | 8/2000 | Roubin et al. | |
| 6,131,266 A | 10/2000 | Saunders | |
| 6,132,461 A | 10/2000 | Thompson | |
| 6,136,006 A | 10/2000 | Johnson et al. | |
| 6,146,403 A | 11/2000 | St. Germain | |
| 6,156,052 A | 12/2000 | Richter et al. | |
| 6,162,231 A | 12/2000 | Mikus et al. | |
| 6,171,334 B1 | 1/2001 | Cox | |
| 6,179,867 B1 | 1/2001 | Cox | |
| 6,183,506 B1 | 2/2001 | Penn et al. | |
| 6,193,744 B1 | 2/2001 | Ehr et al. | |
| 6,203,568 B1 | 3/2001 | Lombardi et al. | |
| 6,217,608 B1 | 4/2001 | Penn et al. | |
| 6,231,598 B1 | 5/2001 | Berry et al. | |
| 6,241,757 B1 | 6/2001 | An et al. | |
| 6,251,134 B1 | 6/2001 | Alt et al. | |
| 6,270,524 B1 | 8/2001 | Kim | |
| 6,273,910 B1 | 8/2001 | Limon | |
| 6,283,992 B1 | 9/2001 | Hankh et al. | |
| 6,293,964 B1 | 9/2001 | Yadav | |
| 6,293,966 B1 | 9/2001 | Frantzen | |
| 6,293,968 B1 | 9/2001 | Taheri | |
| 6,302,906 B1 | 10/2001 | Goicoechea et al. | |
| 6,306,141 B1 | 10/2001 | Jervis | |
| 6,312,459 B1 | 11/2001 | Huang et al. | |
| 6,315,794 B1 | 11/2001 | Richter | |
| 6,322,586 B1 | 11/2001 | Monroe et al. | |
| 6,325,790 B1 | 12/2001 | Trotta | |
| 6,325,821 B1 | 12/2001 | Gaschino et al. | |
| 6,325,825 B1 | 12/2001 | Kula et al. | |
| 6,336,938 B1 | 1/2002 | Kavteladze et al. | |
| 6,348,065 B1 | 2/2002 | Brown et al. | |
| 6,352,552 B1 | 3/2002 | Levinson et al. | |
| 6,355,063 B1 | 3/2002 | Calcote | |
| 6,369,355 B1 | 4/2002 | Saunders | |
| 6,375,676 B1 | 4/2002 | Cox | |
| 6,375,677 B1 | 4/2002 | Penn et al. | |
| 6,409,754 B1 | 6/2002 | Smith et al. | |
| 6,423,084 B1 | 7/2002 | St. Germain | |
| 6,423,091 B1 | 7/2002 | Hojeibane | |
| 6,428,570 B1 | 8/2002 | Globerman | |
| 6,432,133 B1 | 8/2002 | Lau et al. | |
| 6,440,162 B1 | 8/2002 | Cox et al. | |
| 6,443,982 B1 | 9/2002 | Israel et al. | |
| 6,451,025 B1 | 9/2002 | Jervis | |
| 6,451,049 B2 | 9/2002 | Vallana et al. | |
| 6,461,380 B1 | 10/2002 | Cox | |

| | | | | | | |
|---|---|---|---|---|---|---|
| 6,461,381 B2 | 10/2002 | Israel et al. | | 6,692,522 B1 | 2/2004 | Richter |
| 6,464,720 B2 | 10/2002 | Boatman et al. | | 6,695,809 B1 | 2/2004 | Lee |
| 6,464,722 B2 | 10/2002 | Israel et al. | | 6,695,812 B2 | 2/2004 | Estrada et al. |
| 6,471,721 B1 | 10/2002 | Dang | | 6,695,833 B1 | 2/2004 | Frantzen |
| 6,475,236 B1 | 11/2002 | Roubin et al. | | 6,695,862 B2 | 2/2004 | Cox et al. |
| 6,478,815 B1 | 11/2002 | Alt | | 6,695,876 B1 | 2/2004 | Marotta et al. |
| 6,485,524 B2 | 11/2002 | Strecker | | 6,699,274 B2 | 3/2004 | Stinson |
| 6,488,703 B1 | 12/2002 | Kveen et al. | | 6,699,277 B1 | 3/2004 | Freidberg et al. |
| 6,508,834 B1 | 1/2003 | Pinchasik et al. | | 6,699,278 B1 | 3/2004 | Fischell et al. |
| 6,514,285 B1 | 2/2003 | Pinchasik | | 6,702,849 B1 | 3/2004 | Dutta et al. |
| 6,517,569 B2 | 2/2003 | Mikus et al. | | 6,702,850 B1 | 3/2004 | Byun et al. |
| 6,533,805 B1 | 3/2003 | Jervis | | 6,706,061 B1 | 3/2004 | Fischell et al. |
| 6,533,810 B2 | 3/2003 | Hankh et al. | | 6,706,062 B2 | 3/2004 | Vardi et al. |
| 6,540,777 B2 | 4/2003 | Stenzel | | 6,709,440 B2 | 3/2004 | Callol et al. |
| 6,551,351 B2 | 4/2003 | Smith et al. | | 6,709,451 B1 | 3/2004 | Noble et al. |
| 6,569,085 B2 | 5/2003 | Kortenbach et al. | | 6,709,453 B2 | 3/2004 | Pinchasik et al. |
| 6,569,194 B1 | 5/2003 | Pelton | | 6,709,454 B1 | 3/2004 | Cox et al. |
| 6,572,646 B1 | 6/2003 | Boylan et al. | | 6,712,843 B2 | 3/2004 | Elliott |
| 6,589,276 B2 | 7/2003 | Pinchasik et al. | | 6,712,844 B2 | 3/2004 | Pacetti |
| 6,602,285 B1 | 8/2003 | Von Oepen et al. | | 6,716,240 B2 | 4/2004 | Fischell et al. |
| 6,613,078 B1 | 9/2003 | Barone | | 6,719,782 B1 | 4/2004 | Chuter |
| 6,613,079 B1 | 9/2003 | Wolinsky et al. | | 6,723,071 B2 | 4/2004 | Gerdts et al. |
| 6,613,080 B1 | 9/2003 | Lootz | | 6,723,113 B1 | 4/2004 | Shkolnik |
| 6,613,081 B2 | 9/2003 | Kim et al. | | 6,723,118 B1 | 4/2004 | Ballou et al. |
| 6,616,688 B2 | 9/2003 | Von Oepen | | 6,723,119 B2 | 4/2004 | Pinchasik et al. |
| 6,616,689 B1 | 9/2003 | Ainsworth et al. | | 6,723,121 B1 | 4/2004 | Zhong |
| 6,616,690 B2 | 9/2003 | Rolando et al. | | 6,726,712 B1 | 4/2004 | Raeder-Devens et al. |
| 6,620,192 B1 | 9/2003 | Jalisi | | 6,730,116 B1 | 5/2004 | Wolinsky et al. |
| 6,620,193 B1 | 9/2003 | Lau et al. | | 6,730,117 B1 | 5/2004 | Tseng et al. |
| 6,620,201 B1 | 9/2003 | Nadal et al. | | 6,730,120 B2 | 5/2004 | Berg et al. |
| 6,623,491 B2 | 9/2003 | Thompson | | 6,733,521 B2 | 5/2004 | Chobotov et al. |
| 6,623,520 B2 | 9/2003 | Jalisi | | 6,733,523 B2 | 5/2004 | Shaolian et al. |
| 6,635,084 B2 | 10/2003 | Israel et al. | | 6,733,524 B2 | 5/2004 | Tseng et al. |
| 6,638,300 B1 | 10/2003 | Frantzen | | 6,736,828 B1 | 5/2004 | Adams et al. |
| 6,641,608 B1 | 11/2003 | Pulnev | | 6,736,838 B1 | 5/2004 | Richter |
| 6,641,609 B2 | 11/2003 | Globerman | | 6,736,843 B1 | 5/2004 | Fariabi |
| 6,645,242 B1 | 11/2003 | Quinn | | 6,736,844 B1 | 5/2004 | Glatt et al. |
| 6,652,572 B2 | 11/2003 | Kugler et al. | | 6,740,113 B2 | 5/2004 | Vrba |
| 6,652,573 B2 | 11/2003 | von Oepen | | 6,740,114 B2 | 5/2004 | Burgermeister |
| 6,652,575 B2 | 11/2003 | Wang | | 6,740,115 B2 | 5/2004 | Lombardi et al. |
| 6,652,579 B1 | 11/2003 | Cox et al. | | 6,743,219 B1 | 6/2004 | Dwyer et al. |
| 6,656,201 B2 | 12/2003 | Ferrera et al. | | 6,743,252 B1 | 6/2004 | Bates et al. |
| 6,656,211 B1 | 12/2003 | DiCaprio | | 6,746,423 B1 | 6/2004 | Wantink |
| 6,656,214 B1 | 12/2003 | Fogarty et al. | | 6,746,475 B1 | 6/2004 | Rivelli, Jr. |
| 6,656,216 B1 | 12/2003 | Hossainy et al. | | 6,746,476 B1 | 6/2004 | Hojeibane |
| 6,656,220 B1 | 12/2003 | Gomez et al. | | 6,746,477 B2 | 6/2004 | Moore |
| 6,660,019 B1 | 12/2003 | Richter et al. | | 6,746,479 B2 | 6/2004 | Ehr et al. |
| 6,660,034 B1 | 12/2003 | Mandrusov et al. | | 6,749,627 B2 | 6/2004 | Thompson et al. |
| 6,663,660 B2 | 12/2003 | Dusbabek et al. | | 6,749,629 B1 | 6/2004 | Hong et al. |
| 6,663,664 B1 | 12/2003 | Pacetti | | 6,752,819 B1 | 6/2004 | Brady et al. |
| 6,663,880 B1 | 12/2003 | Roorda et al. | | 6,752,825 B2 | 6/2004 | Eskuri |
| 6,664,335 B2 | 12/2003 | Krishnan | | 6,755,855 B2 | 6/2004 | Yurek et al. |
| 6,666,881 B1 | 12/2003 | Richter et al. | | 6,755,856 B2 | 6/2004 | Fierens et al. |
| 6,666,884 B1 | 12/2003 | Webster | | 6,756,007 B2 | 6/2004 | Pletzer et al. |
| 6,669,716 B1 | 12/2003 | Gilson et al. | | 6,758,860 B1 | 7/2004 | Penn et al. |
| 6,669,718 B2 | 12/2003 | Besselink | | 6,761,703 B2 | 7/2004 | Miller et al. |
| 6,669,720 B1 | 12/2003 | Pierce | | 6,761,708 B1 | 7/2004 | Chiu et al. |
| 6,669,722 B2 | 12/2003 | Chen et al. | | 6,761,731 B2 | 7/2004 | Majercak |
| 6,669,723 B2 | 12/2003 | Killion et al. | | 6,761,733 B2 | 7/2004 | Chobotov et al. |
| 6,673,101 B1 | 1/2004 | Fitzgerald et al. | | 6,764,505 B1 | 7/2004 | Hossainy et al. |
| 6,673,104 B2 | 1/2004 | Barry | | 6,764,506 B2 | 7/2004 | Roubin et al. |
| 6,673,106 B2 | 1/2004 | Mitelberg et al. | | 6,764,507 B2 | 7/2004 | Shanley et al. |
| 6,673,107 B1 | 1/2004 | Brandt et al. | | 6,764,519 B2 | 7/2004 | Whitmore, III |
| 6,676,692 B2 | 1/2004 | Rabkin et al. | | 6,770,088 B1 | 8/2004 | Jang |
| 6,676,693 B1 | 1/2004 | Belding et al. | | 6,770,089 B1 | 8/2004 | Hong et al. |
| 6,676,697 B1 | 1/2004 | Richter | | 6,770,091 B2 | 8/2004 | Richter et al. |
| 6,679,910 B1 | 1/2004 | Granada | | 6,773,445 B2 | 8/2004 | Finlay et al. |
| 6,679,911 B2 | 1/2004 | Burgermeister | | 6,773,446 B1 | 8/2004 | Dwyer et al. |
| 6,682,554 B2 | 1/2004 | Oepen et al. | | 6,773,447 B2 | 8/2004 | Laguna |
| 6,689,157 B2 | 2/2004 | Madrid et al. | | 6,773,448 B2 | 8/2004 | Kusleika et al. |
| 6,689,162 B1 | 2/2004 | Thompson | | 6,776,022 B2 | 8/2004 | Kula et al. |
| 6,692,483 B2 | 2/2004 | Vardi et al. | | 6,776,793 B2 | 8/2004 | Brown et al. |
| 6,692,521 B2 | 2/2004 | Pinchasik | | 6,776,794 B1 | 8/2004 | Hong et al. |

| Patent Number | Date | Name |
|---|---|---|
| 6,776,795 B2 | 8/2004 | Pelton |
| 6,780,182 B2 | 8/2004 | Bowman et al. |
| 6,780,199 B2 | 8/2004 | Solar et al. |
| 6,790,220 B2 | 9/2004 | Morris et al. |
| 6,790,222 B2 | 9/2004 | Kugler et al. |
| 6,790,223 B2 | 9/2004 | Reever |
| 6,790,227 B2 | 9/2004 | Burgermeister |
| 6,796,997 B1 | 9/2004 | Penn et al. |
| 6,800,081 B2 | 10/2004 | Parodi |
| 6,802,846 B2 | 10/2004 | Hauschild et al. |
| 6,802,849 B2 | 10/2004 | Blaeser et al. |
| 6,802,859 B1 | 10/2004 | Pazienza et al. |
| 6,805,704 B1 | 10/2004 | Hoyns |
| 6,805,705 B2 | 10/2004 | Hong et al. |
| 6,805,706 B2 | 10/2004 | Solovay et al. |
| 6,805,707 B1 | 10/2004 | Hong et al. |
| 6,808,529 B2 | 10/2004 | Fulkerson |
| 6,808,533 B1 | 10/2004 | Goodwin et al. |
| 6,814,749 B2 | 11/2004 | Cox et al. |
| 6,818,013 B2 | 11/2004 | Mitelberg et al. |
| 6,818,014 B2 | 11/2004 | Brian et al. |
| 6,818,015 B2 | 11/2004 | Hankh et al. |
| 6,818,247 B1 | 11/2004 | Chen et al. |
| 6,821,291 B2 | 11/2004 | Bolea et al. |
| 6,821,292 B2 | 11/2004 | Pazienza et al. |
| 6,821,293 B2 | 11/2004 | Pinchasik |
| 6,830,638 B2 | 12/2004 | Boylan et al. |
| 6,833,004 B2 | 12/2004 | Ishii et al. |
| 6,843,802 B1 | 1/2005 | Villalobos et al. |
| 6,849,086 B2 | 2/2005 | Cragg |
| 6,852,124 B2 | 2/2005 | Cox et al. |
| 6,858,037 B2 | 2/2005 | Penn et al. |
| 6,860,898 B2 | 3/2005 | Stack et al. |
| 6,860,900 B2 | 3/2005 | Clerc et al. |
| 6,863,684 B2 | 3/2005 | Kim et al. |
| 6,866,805 B2 | 3/2005 | Hong et al. |
| 6,875,227 B2 | 4/2005 | Yoon |
| 6,878,162 B2 | 4/2005 | Bales et al. |
| 6,881,221 B2 | 4/2005 | Golds |
| 6,881,222 B2 | 4/2005 | White et al. |
| 6,881,223 B2 | 4/2005 | Penn et al. |
| 6,887,264 B2 | 5/2005 | Penn et al. |
| 6,896,696 B2 | 5/2005 | Doran et al. |
| 6,896,697 B1 | 5/2005 | Yip et al. |
| 6,896,698 B2 | 5/2005 | Rolando et al. |
| 6,899,729 B1 | 5/2005 | Cox et al. |
| 6,908,624 B2 | 6/2005 | Hossainy et al. |
| 6,911,041 B1 | 6/2005 | Zscheeg |
| 6,916,336 B2 | 7/2005 | Patel et al. |
| 6,920,677 B2 | 7/2005 | Dolan et al. |
| 6,955,723 B2 | 10/2005 | Pacetti et al. |
| 6,979,348 B2 | 12/2005 | Sundar |
| 7,004,966 B2 | 2/2006 | Edwin et al. |
| 2001/0016767 A1 | 8/2001 | Wilson et al. |
| 2001/0016768 A1 | 8/2001 | Wilson et al. |
| 2001/0027339 A1 | 10/2001 | Boatman et al. |
| 2001/0037138 A1 | 11/2001 | Wilston et al. |
| 2002/0042650 A1 | 4/2002 | Vardi et al. |
| 2002/0111672 A1 | 8/2002 | Kim et al. |
| 2002/0156524 A1 | 10/2002 | Ehr et al. |
| 2002/0161425 A1 | 10/2002 | Hemerick et al. |
| 2002/0183763 A1 | 12/2002 | Callot et al. |
| 2002/0183831 A1 | 12/2002 | Rolando et al. |
| 2002/0183832 A1 | 12/2002 | Penn et al. |
| 2002/0188344 A1 | 12/2002 | Bolea et al. |
| 2002/0193866 A1 | 12/2002 | Saunders |
| 2002/0198593 A1 | 12/2002 | Gomez et al. |
| 2003/0004567 A1 | 1/2003 | Boyle et al. |
| 2003/0036793 A1 | 2/2003 | Richter et al. |
| 2003/0045925 A1 | 3/2003 | Jayaraman |
| 2003/0050690 A1 | 3/2003 | Kveen et al. |
| 2003/0077310 A1 | 4/2003 | Pathak et al. |
| 2003/0083734 A1 | 5/2003 | Friedrich et al. |
| 2003/0105511 A1 | 6/2003 | Welsh et al. |
| 2003/0105513 A1 | 6/2003 | Moriuchi et al. |
| 2003/0114919 A1 | 6/2003 | McQuiston et al. |
| 2003/0125799 A1 | 7/2003 | Limon |
| 2003/0139796 A1 | 7/2003 | Sequin et al. |
| 2003/0144671 A1 | 7/2003 | Brooks et al. |
| 2003/0144726 A1 | 7/2003 | Majercak et al. |
| 2003/0144731 A1 | 7/2003 | Wolinsky et al. |
| 2003/0149469 A1 | 8/2003 | Wolinsky et al. |
| 2003/0158596 A1 | 8/2003 | Ikeuchi et al. |

FOREIGN PATENT DOCUMENTS

| | | |
|---|---|---|
| DE | 197 03 482 A1 | 8/1998 |
| DE | 101 18 944 A1 | 10/2002 |
| EP | 0 183 372 | 10/1984 |
| EP | 0 350 302 A1 | 1/1990 |
| EP | 0 378 151 A2 | 7/1990 |
| EP | 0 382 014 A1 | 8/1990 |
| EP | 0 540 290 A2 | 10/1991 |
| EP | 0 516 189 A1 | 12/1992 |
| EP | 0 540 290 A2 | 5/1993 |
| EP | 0 621 015 A1 | 10/1994 |
| EP | 0 847 733 B1 | 6/1998 |
| EP | 0 945 107 A2 | 1/1999 |
| EP | 1 093 771 A2 | 4/2001 |
| EP | 1 208 814 A2 | 9/2001 |
| GR | 92100104 | 3/1992 |
| JP | 10-272190 | 10/1998 |
| JP | 11-57022 | 3/1999 |
| RU | 2 186 547 | 4/2000 |
| WO | WO 91/13384 | 9/1991 |
| WO | WO 92/11824 | 7/1992 |
| WO | WO 93/22986 | 11/1993 |
| WO | WO 94/21196 | 9/1994 |
| WO | WO 94/22379 A | 10/1994 |
| WO | WO 97/14456 | 4/1997 |
| WO | WO 97/40739 | 11/1997 |
| WO | WO 99/62430 | 12/1999 |
| WO | WO 00/44308 | 8/2000 |
| WO | WO 00/44308 A | 8/2000 |
| WO | WO 01/76508 A2 | 10/2001 |
| WO | WO 02/083038 A2 | 10/2002 |

* cited by examiner

REMOVABLE ESSENTIALLY CYLINDRICAL IMPLANTS

CROSS REFERENCE TO RELATED APPLICATIONS

The present application is a National Stage of International Application No. PCT/DE02/01244 filed Apr. 5, 2002, which claims priority from German Patent No. DE 10118944 filed Apr. 18, 2001, the contents of which are incorporated herein by reference.

BACKGROUND OF THE INVENTION

The invention relates to removable, essentially cylindrical implants.

Occasionally, for various reasons, such implants, i.e. predominantly so-called stents, must be removed from the body after the surgical procedure. In many cases, this causes problems as newly formed tissue grows to and—depending on the structure—also through the implants so that the removal may cause complications.

SUMMARY OF THE INVENTION

There is thus a need to so configure cylindrical implants of this type as to allow a removal from the body in a simple manner with as little complication as possible.

Surprisingly, it has been found that the difficulties experienced heretofore during removal of respective implants can be overcome in a relative simple manner when these implants can be reduced in diameter and are wrapped by one or more thin, flexible wire-shaped structures, in the following designated as wire for sake of simplicity, and when this wire has on at least one end a catch device in which an appropriate surgical instrument can engage or which can be embraced by such an instrument. By pulling the catch device, the diameter of the implant is reduced by the wire at one or more levels of the entire implant so that the implant detaches from the tissue or from the tissue walls and can be withdrawn.

The implants according to the invention, i.e. stents in particular, are made of lattice-shaped or mesh-shaped physiologically compatible metal or plastic and are oftentimes provided on one side with an open groove so as to be compressible in the latter case, but otherwise extendible, to therefore ensure a reduction in diameter. This is attained in accordance with the invention by providing one or more wires of metal or plastic which is/are thin and flexible, wrapped at least at one level of the implant about the implant and normally secured, for safety reasons, to one end of the implant by, e.g., typical fastening techniques such as welding, entwining, knotting, or similar manner. It is, of course, also possible to eliminate in certain cases the need for such a securement, when the wire is wrapped several times about the implant at one level and thus is prevented from sliding off. At least one end of the wire or wires is provided with a catch device which may be configured, for example, as thickened end for embracement by a surgical instrument or as eyelet or loop for engagement with an appropriate instrument.

According to a preferred embodiment, the implant is wrapped by at least 2 wires which are wound in form of a helix about the implant and whose two free ends, i.e. the ends that are not affixed, include a respective catch device.

In any event, it is important that the catch device is provided at a time when the implant is constructed, i.e. there should not be a requirement to later place a loop about the implant, but the catch device is already provided or incorporated during production of the implant. The wire may freely run about the implant, in particular when wound several times, or it may run in guide eyelets which are arranged on the outside, inside or in the wall of the implant. Optionally, the wire may also extend between the braiding or lattice of the implant and an outer jacket. When attaching the loop on the outside, the implant is pressed together or constricted, in particular when the implant has a groove. When arranging the pull wire on the inside, the stent collapses. Important in any event is the reduction of the axial diameter by the longitudinal pull so that the implant is able to gently detach from the tissue.

The wire construction may extend over the entire length of the stent or only at the upper end. Optionally, the wire construction may also extend through the lumen of the stent, then crosswise for example.

When metal implants or the use of metal wires are involved, the construction is preferably configured such that they can be captured through visualization using endoscopy or through use of X-ray control without direct visualization.

The construction according to the invention significantly simplifies the removal of cylindrical implants as the removal is significantly less time-consuming and less complicated.

BRIEF DESCRIPTION THE DRAWING

Figure 2:
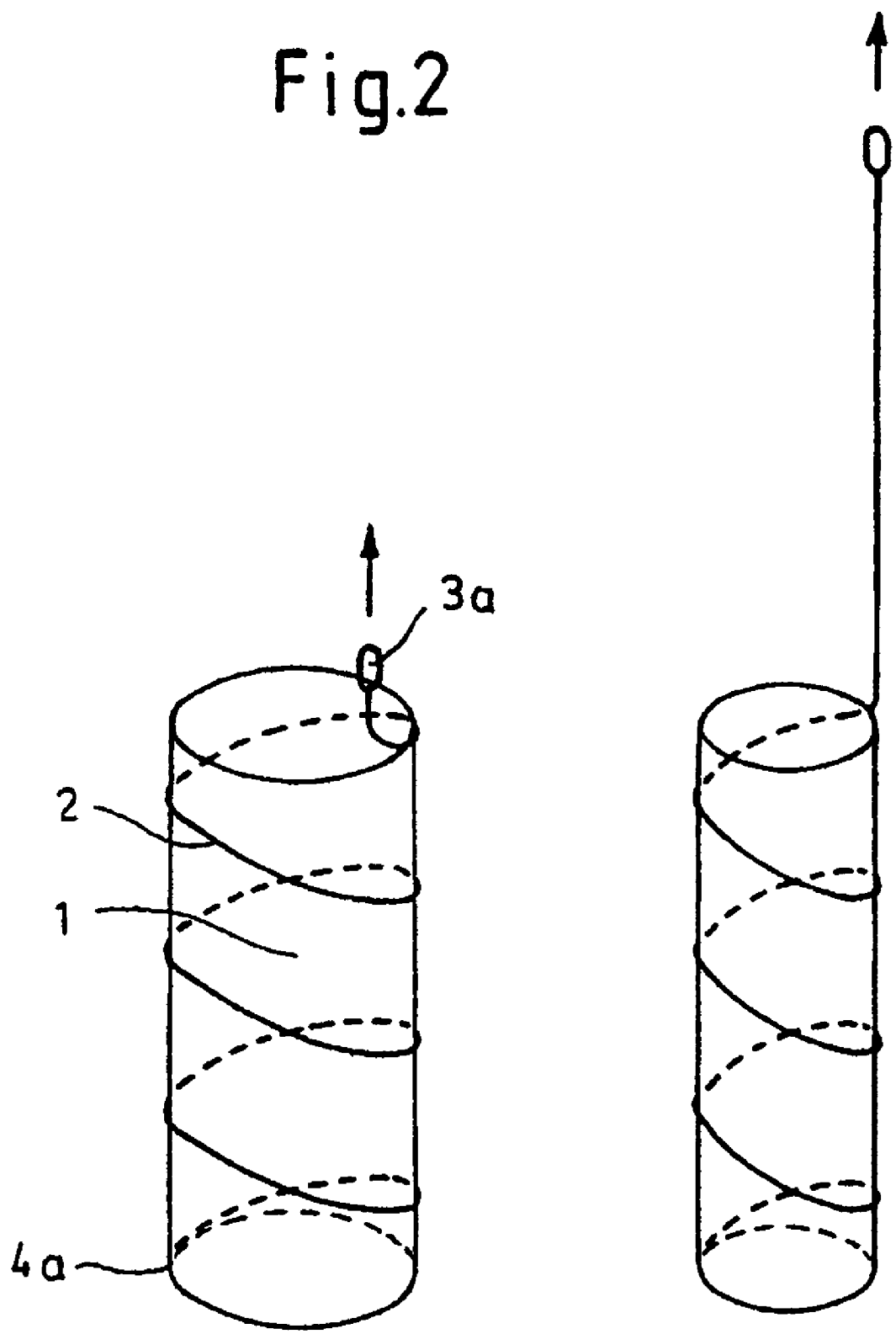
Figure 3:
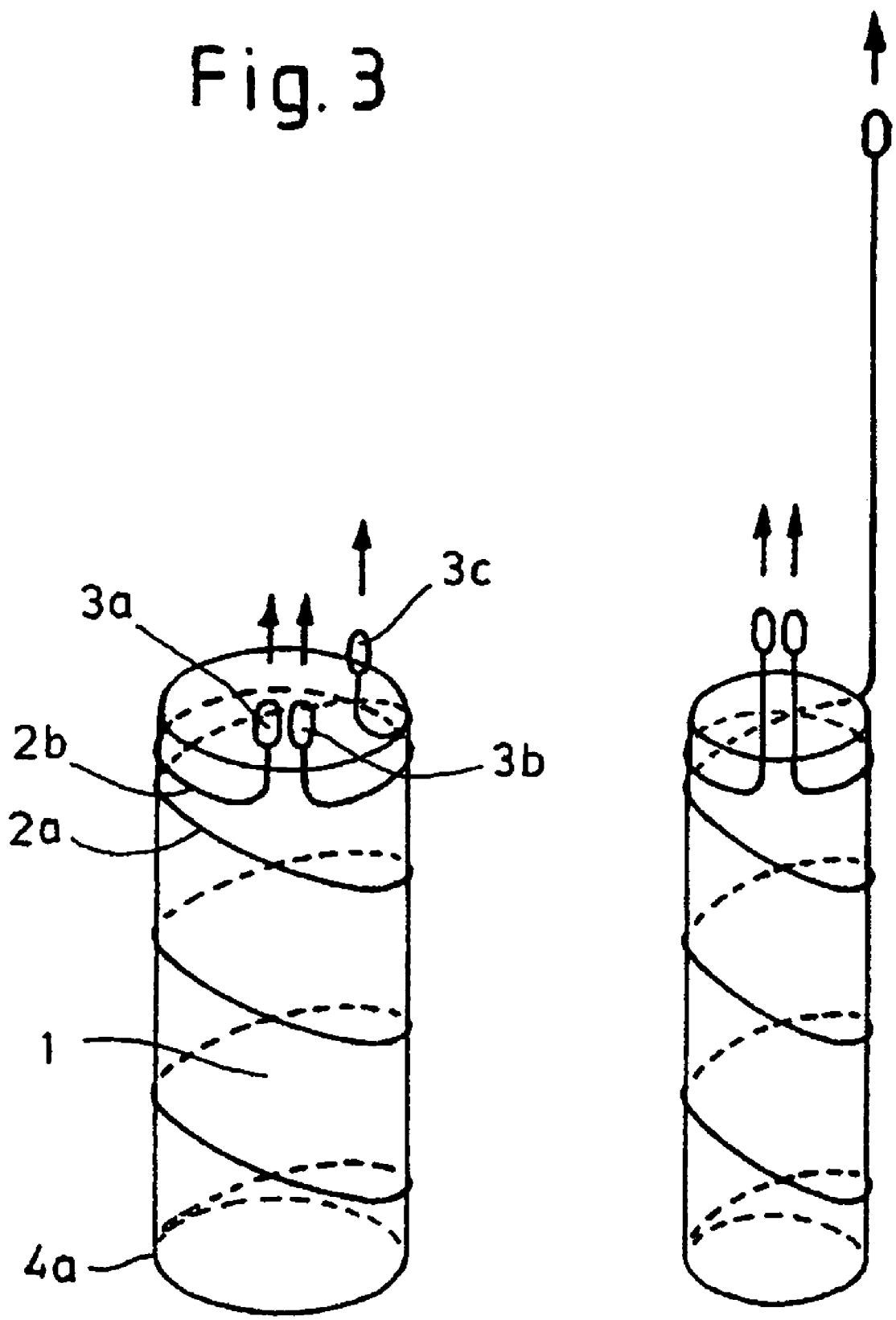
Figure 4:
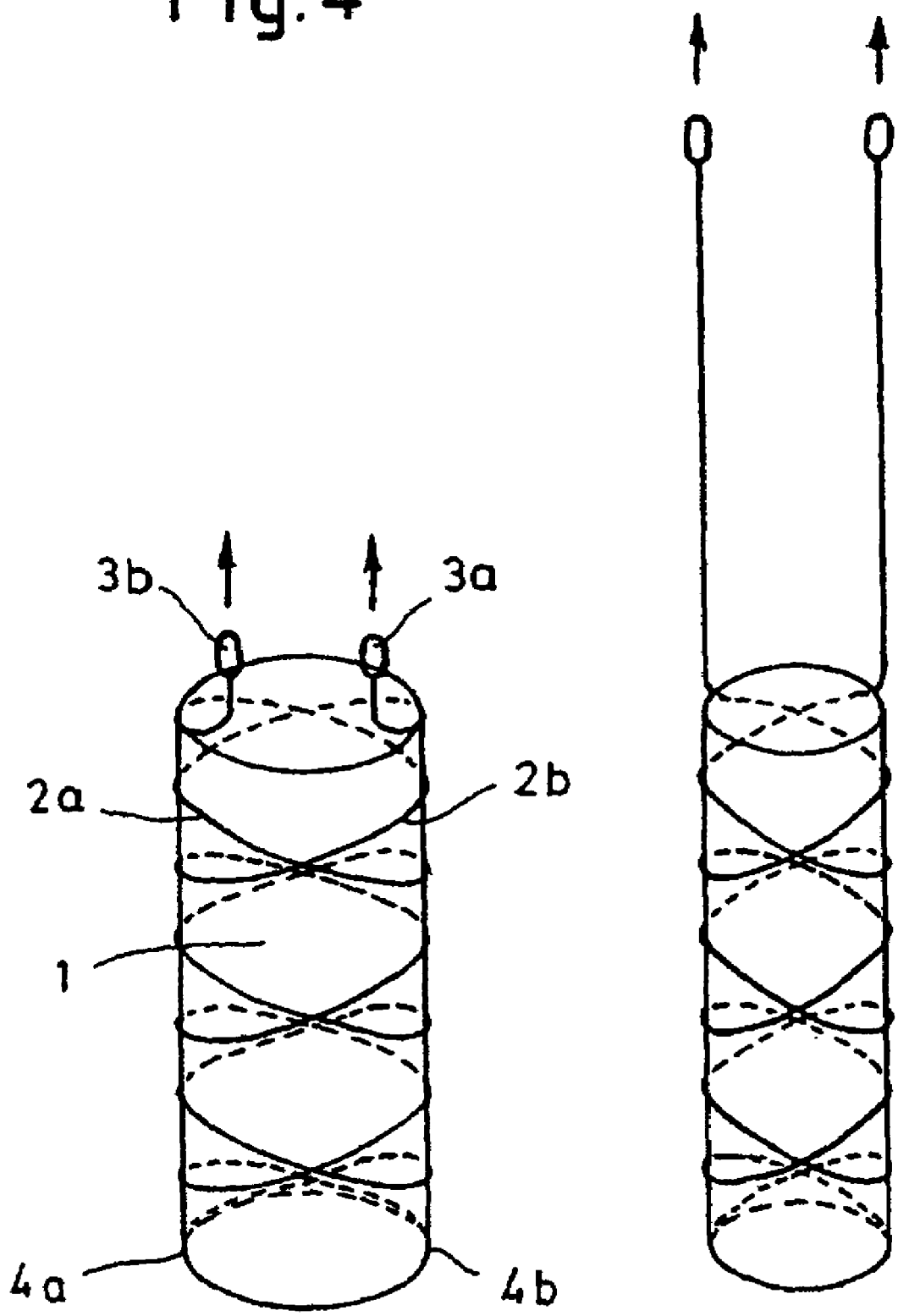

The invention will now be described in more detail with reference to the drawing, in which:

FIG. 1 shows a schematic illustration of an implant according to the invention with a single loop on one end, FIG. 2 shows a schematic illustration of an implant with a helical loop as single loop, FIG. 3 shows a schematic illustration of an implant with a helical loop as single loop and a single loop at the end, FIG. 4 shows also a schematic illustration of an implant with helical loops as double-loop.

Figure 5:
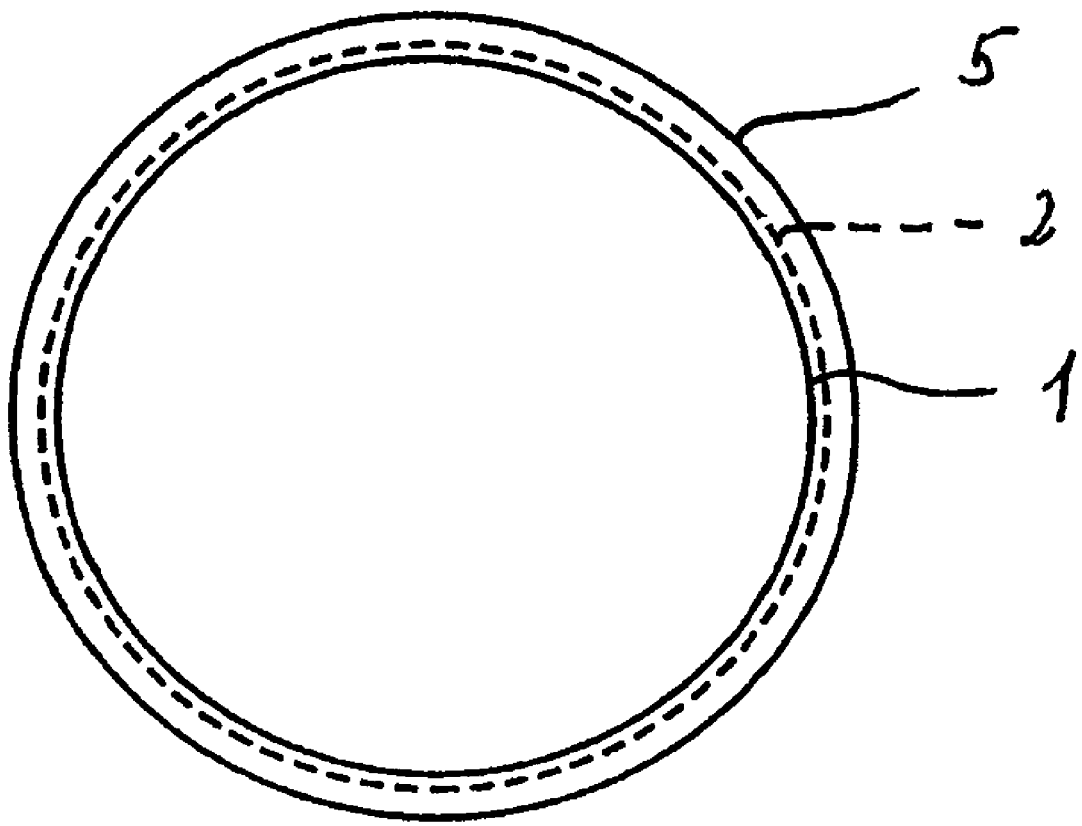

FIG. 5 shows a schematic illustration of an implant surrounded by a jacket.

DETAILED DESCRIPTION OF PREFERRED EMBODIMENTS

The implant 1 of substantially cylindrical shape is wrapped either on one end with a wire-shaped single loop which may be secured either to the outer wall of the implant or is wrapped several times about the implant. This wire-shaped loop 2a has on each end a catch device 3a and 3b, respectively, which cause at least partially a reduction in diameter of the implant when being pulled in direction of the indicated arrows.

Instead of a single loop, the wire may also be configured as helical loop 2, as shown in FIG. 2, which includes a catch device 3a and is secured to the end 4a of the implant such that a reduction in the overall diameter of the implant is realized when pulling in the indicated arrow direction.

As shown in FIG. 3, it is also possible to combine a helical loop and a single loop with one another, by providing the implant 1, on one hand, with a helical loop 2a which is secured on the end 4a, and on the other hand, with a single loop 2b, whereby both loops are provided with catch devices 3a, 3b and 3c. Thus, the overall diameter is reduced when pulling, whereby the reduction is more pronounced at the upper end where the additional single loop 2b is positioned than in the remaining portion.

According to a preferred embodiment, as shown in FIG. 4, the implant 1 has two helical loops 2a and 2b, which are secured at the ends 4a and 4b of the implant and terminate in catch devices 3a and 3b. The double helical loop is able to attain a particularly pronounced reduction in diameter of the implant.

As shown in FIG. 5, the wire 2 may also extend between the braiding or lattice of the implant 1 and an outer jacket 5.

What is claimed is:

1. A removable implant, comprising an implant body;
   at least one flexible, thin wire-shaped structure having a portion slidably wrapped at least once about the implant body; and
   a catch device provided on an end of the structure, said slidable portion of the structure configured to shorten as the catch device is pulled in the longitudinal direction;
   wherein the implant body is reducible in diameter, at least partially by pulling the catch device in a longitudinal direction and shortening the slidable portion of the structure wrapped about the implant body.

2. The implant of claim 1, wherein the slidable portion of the structure is wrapped more than once about the implant body.

3. The implant of claim 1, wherein the slidable portion of the structure is wrapped several times about the implant body at one level only.

4. The implant of claim 1, wherein the slidable portion of the structure is wrapped several times about the implant body at several levels.

5. The implant of claim 1, wherein the implant body is made of a lattice or mesh of metal or plastic.

6. The implant of claim 1, wherein the implant body includes an open groove.

7. The implant of claim 1, wherein the structure is made of metal or plastic.

8. The implant of claim 1, wherein the structure has at least one end secured on or in the implant.

9. The implant of claim 1, wherein the catch device is configured as one member selected from the group consisting of thickened end, eyelet and loop.

10. The implant of claim 1, wherein the slidable portion of the structure is wrapped about the implant body at a single level only.

11. The implant of claim 1, wherein the slidable portion of the structure is wrapped about the implant body in a helical manner.

12. The implant of claim 1, wherein the structure extends between the implant body and an outer jacket.

13. The implant of claim 1, wherein the structure extends over an entire length of the implant body.

14. The implant of claim 1, wherein the structure extends only at an upper end of the implant body.

15. The implant of claim 1, wherein the implant can be captured through use of X-ray control without direct visualization.

16. The implant of claim 1, wherein the structure is secured to the implant body by a process selected from the group consisting of welding, entwining and knotting.

* * * * *